Sept. 10, 1974 A. W. FISCHER Plant Pat. 3,611
VIOLET PLANT
Filed May 3, 1973
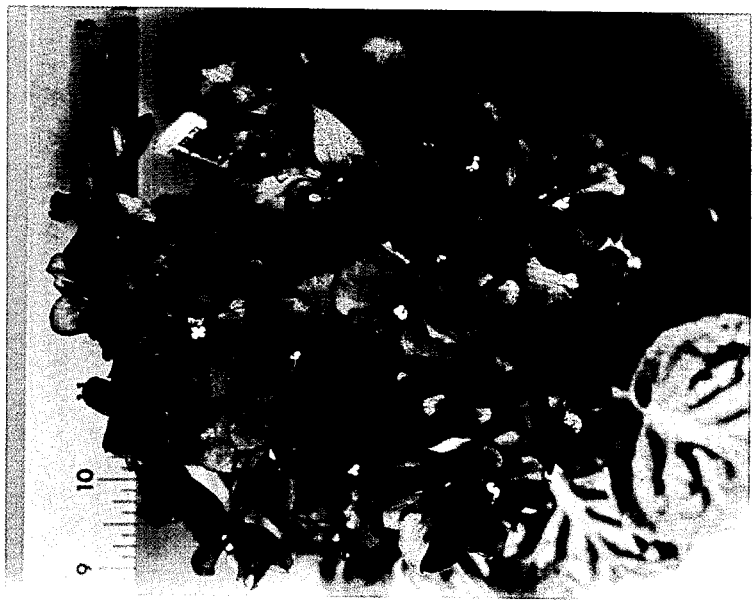
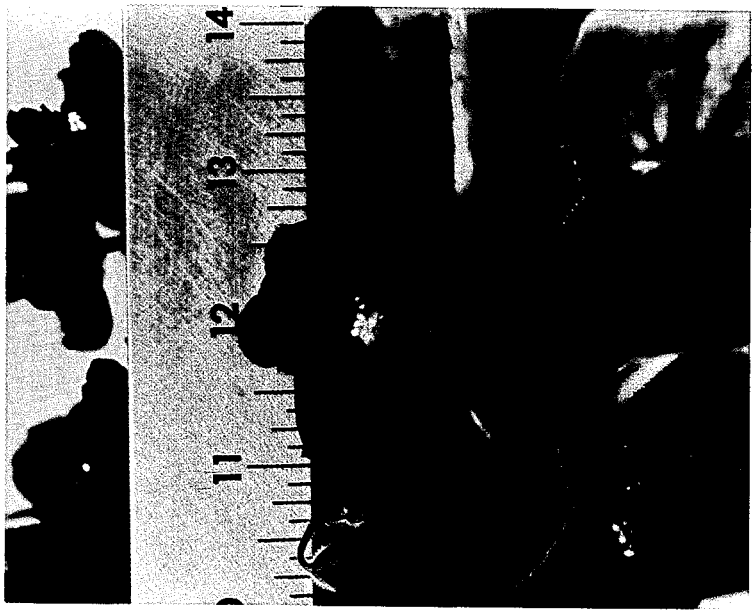

United States Patent Office

Plant Pat. 3,611

Patented Sept. 10, 1974

3,611

VIOLET PLANT

Arnold W. Fischer, Isernhagen, Germany, assignor to Geo. J. Ball, Inc., West Chicago, Ill.

Filed May 3, 1973, Ser. No. 356,926

Int. Cl. A01h *5/00*

U.S. Cl. Plt.—69 1 Claim

ABSTRACT OF THE DISCLOSURE

A new variety of African violet plant distinguished by the unique deep violet color of its blossoms which bloom profusely and form clusters of large long-lasting flowers; and by its vigorous growth, early flowering habit, and its tolerance for environmental changes.

BACKGROUND OF THE INVENTION

My new variety of African violet originated as a greenhouse seedling at Isernhagen, Germany, resulting from breeding efforts carried on by me since 1963 with the object of producing new plants which produce flowers of improved coloring and lasting quality; and which grow rapidly and reproduce readily. This plant was selected by me for propagation because it appeared to have characteristics of the kind I was seeking and asexual reproduction of this plant by leaf cuttings under my supervision at Isernhagen, Germany, has demonstrated that its distinguishing characteristics are firmly fixed and hold true from generation to generation. Commercial propagation of this new plant, by leaf cuttings and division of shoots, has been carried on at West Chicago, Ill., U.S.A., for more than a year and this has also shown my new variety of African violet to have its novel characteristics firmly fixed and holding true from generation to generation.

DESCRIPTION OF THE DRAWING

My new variety of African violet is illustrated by the accompanying drawing which shows the color characteristics and form of the plant and its flowers, the color reproduction being as nearly true as is reasonably possible to be done, by conventional photographic methods. The right hand view shows a potted group of the plant and demonstrates the manner in which the flower clusters converge to form a dense head; and the left hand view shows a close-up of one of the fully opened flowers, as well as a few buds just beginning to show color.

DESCRIPTION OF THE NEW PLANT

The following is a detailed description of my new African violet plant with color designations according to the Horticultural Colour Chart (HCC) produced by Robert F. Wilson and published in collaeboration with The Royal Horticultural Society of London, England.

THE PLANT

Origin: Seedling.

Parentage:

*Seed Parent.*—#069–1, a blue double, unnamed and unpatented.

*Pollen Parent.*—#66–1, a single blue, unnamed and unpatented.

These parent plants exist among my collection of violet plants maintained for breeding purposes and are identified in my records by the stated numbers.

Classification:

*Botanic—Saintpaulia ionantha*

*Commercial.*—African violet.

Form: Compact potted plant (rosette arrangement).

Height: About 3½ to 4 inches from soil level to top of flowers.

Growth: Vigorous and condensed; sturdy, upright and fairly strong.

Foliage: Not very compact and number of leaves varies from plant to plant.

*Size of Leaf.*—Mature leaf—2⅛ inches long x 2 inches wide.

*Shape of Leaf.*—Almost circular.

*Texture.*—Tomentose on both sides, with crenate margins having broad rounded teeth.

*Ribs and Veins.*—Pinnately veined, pronounced on underside.

*Color.*—Upper side—Spinach Green 0960., Under side—Pod Green 061/3.

*Petioles.*—Length varies with age of plant. In a mature plant petioles are up to 2¾ inches long.

THE BUD

Form: Spherical, wide bell-shaped when sepals open.

Size: Just before opening—⅜ inch wide and ¼ inch deep.

Opening Rate: Very slow. Four to five weeks from visible bud until color shows. Then, within two weeks, bud opens into flower.

*Color*: When sepals first divide—Victoria Violet 738/1.

Sepals: Five in number, hooded over bud only for a short time after color first shows. Then sepals stand up and are spear shaped.

*Color.*—Inside and outside—Fern Green 0862/2.

Calyx: Splits to star shape.

*Aspect.*—Smooth on inside, tomentose on outer side.

Peduncle.—Stem length—1⅜ to 2⅛ inches from base (soil) to branching. Flower peduncle—¾ to 1⅛ inches long.

*Strength.*—Flexible and fairly erect.

*Color.*—Maroon 1030.

THE FLOWER

Blooming Habit: Recurrent. Plant blooms early, profusely and the year around.

Size of Flower: Medium to large—15/16 to 1½ inches in diameter and ¼ to ½ inch in depth.

Shape of Flower: When first opening—Generally flat with petaloids held higher. Shape becomes flatter as flower matures.

Borne: Several flowers in cluster on one stem and several stems on one plant.

Petalage: Five petals, plus many petaloids.

*Arrangement.*—Sympetalous.

*Form.*—Generally circular with irregular but smooth marginal edges.

*Texture.*—Soft. Tomentose on underside.

*Appearance.*—Shiny. Almost glitters.

*Color.*—

| | Mature Young Flower (semi-double) | Old Flower |
|---|---|---|
| Face Side: | | |
| Top Petals and Petaloids. | Aconite Violet 937/3 | Victoria Violet 738/3. |
| Lower Petals | Victoria Violet 738/3 to 738/2. | Aster Violet 38. |
| Reverse Side | Sea Lavender Violet 637/1. | Sea Lavender Violet 637/1. |

*Discoloration (After Full Bloom).*—Color fades somewhat.

Petaloids: 4 to 8 in number. ⅛ to ⅜ inch in size and Victoria Violet 738/1 in color.

Peduncle: Stem to flower—¾ to 1⅛ inches long.

*Strength.*—Sturdy and upright.

*Color.*—Maroon 1030/2.

Effect of Weather: Hot weather fades flowers and suppresses flowering. Plant thrives in 80% to 90% humidity.

Persistence: Petals do not drop. Flowers hang on and dry.

Disease Resistance: This plant is resistant to commonly known diseases as observed in environments where such diseases are present.

Fragrance: None

Lasting Quality: 14 to 18 days as a fully opened flower.

REPRODUCTIVE ORGANS

Stamens:

*Anthers.*—Two in number, each composed of two anther cells, in basi-fixed arrangement. Some stamens become petaloids.

*Filament.*—⅛ inch long.

*Color.*—Victoria Violet 738/1.

Pistils: One only.

*Stigma.*—Color—Aster Violet 38/1.

*Style.*—Up to 5/16 inch long. Color—Aster Violet 38/3

Ovary: Tomentose superior.

This new variety of African violet plant is particularly distinguished by the unique color of its profusely produced and long lasting flowers. This plant also has the advantage of being more tolerant of environmental changes than similar varieties, as well as being a vigorously growing, early flowering variety having very good commercial value as a year around blooming house plant.

I claim:

1. A new variety of African violet plant, substantially as herein shown and described, characterized by its early blooming and vigorously growing habit, its tolerance to environmental changes, its year around blooming capability, and the lasting quality of its fully opened flowers.

No references cited.

ROBERT E. BAGWILL, Primary Examiner